US011089961B2

(12) United States Patent
Ellis et al.

(10) Patent No.: US 11,089,961 B2
(45) Date of Patent: Aug. 17, 2021

(54) SYSTEM AND METHOD FOR MONITORING CORE BODY TEMPERATURE

(71) Applicant: James Foody, County Sligo (IE)

(72) Inventors: Nathan Ellis, Glanmire (IE); Josef Tugwell, Glanmire (IE)

(73) Assignee: James Foody, County Sligo (IE)

( * ) Notice: Subject to any disclaimer, the term of this patent is extended or adjusted under 35 U.S.C. 154(b) by 496 days.

(21) Appl. No.: 15/682,138

(22) Filed: Aug. 21, 2017

(65) Prior Publication Data

US 2018/0049646 A1 Feb. 22, 2018

Related U.S. Application Data

(60) Provisional application No. 62/532,306, filed on Jul. 13, 2017, provisional application No. 62/377,526, filed on Aug. 19, 2016.

(51) Int. Cl.
| | | |
|---|---|---|
| *A61B 5/01* | (2006.01) | |
| *G01K 13/20* | (2021.01) | |
| *A61B 5/00* | (2006.01) | |
| *G01K 1/16* | (2006.01) | |

(52) U.S. Cl.
CPC .............. *A61B 5/01* (2013.01); *A61B 5/0008* (2013.01); *A61B 5/7282* (2013.01); *G01K 1/16* (2013.01); *G01K 13/20* (2021.01); *A61B 2560/0214* (2013.01); *A61B 2560/0412* (2013.01); *A61B 2562/0271* (2013.01); *A61B 2562/04* (2013.01)

(58) Field of Classification Search
CPC ............. A61B 2562/0271; A61B 5/01; G01K 13/002; G01K 1/20
See application file for complete search history.

(56) References Cited

U.S. PATENT DOCUMENTS

| | | |
|---|---|---|
| 6,220,750 B1 | 4/2001 | Palti |
| 6,499,877 B2 | 12/2002 | Pompei |
| 6,821,249 B2 | 11/2004 | Casscells et al. |
| 6,827,487 B2 | 12/2004 | Baumbach |
| 7,785,266 B2 | 8/2010 | Fraden |
| 8,845,187 B2 | 9/2014 | Klewer et al. |
| 2002/0114375 A1 | 8/2002 | Pompei |
| 2004/0076215 A1 | 4/2004 | Baumbach |
| 2007/0055171 A1 | 3/2007 | Fraden |
| 2007/0161921 A1 | 7/2007 | Rausch |
| 2007/0191729 A1 | 8/2007 | Park et al. |
| 2008/0071189 A1 | 3/2008 | Yarden et al. |
| 2009/0016404 A1 | 1/2009 | Wang et al. |
| 2009/0306536 A1 | 12/2009 | Ranganathan et al. |

(Continued)

FOREIGN PATENT DOCUMENTS

WO WO-2013121762 A1 * 8/2013 ............. G01K 1/165

*Primary Examiner* — Puya Agahi
(74) *Attorney, Agent, or Firm* — Jeffrey Schox

(57) ABSTRACT

Embodiments of a system can include a temperature monitoring device including: a heat flux channel, a first temperature sensor thermally coupled to the heat flux channel, a second temperature sensor thermally coupled to the heat flux channel, a thermal cage thermally coupled to and arranged around the heat flux channel along a length of the heat flux channel, and a processing system operable to determine a core body temperature measurement based on temperature data collected at the first and the second temperature sensors.

8 Claims, 10 Drawing Sheets

(56) References Cited

U.S. PATENT DOCUMENTS

| | | |
|---|---|---|
| 2009/0306638 A1* | 12/2009 | Hillely .................... A61B 5/01 |
| | | 606/21 |
| 2011/0317737 A1 | 12/2011 | Klewer et al. |
| 2012/0128024 A1* | 5/2012 | Tsuchida .............. G01K 13/002 |
| | | 374/29 |
| 2014/0169400 A1 | 6/2014 | Baarman et al. |
| 2015/0305688 A1 | 10/2015 | Rath et al. |
| 2015/0313484 A1 | 11/2015 | Burg et al. |
| 2016/0313193 A1 | 10/2016 | Nakagawa et al. |
| 2017/0016778 A1 | 1/2017 | Nakagawa et al. |

* cited by examiner

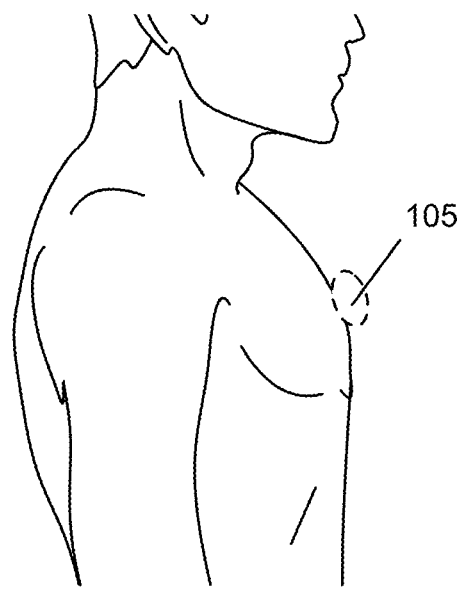
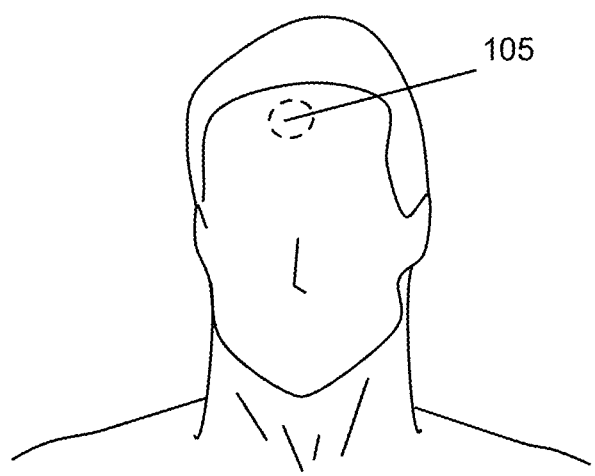
FIGURE 2A
FIGURE 2B
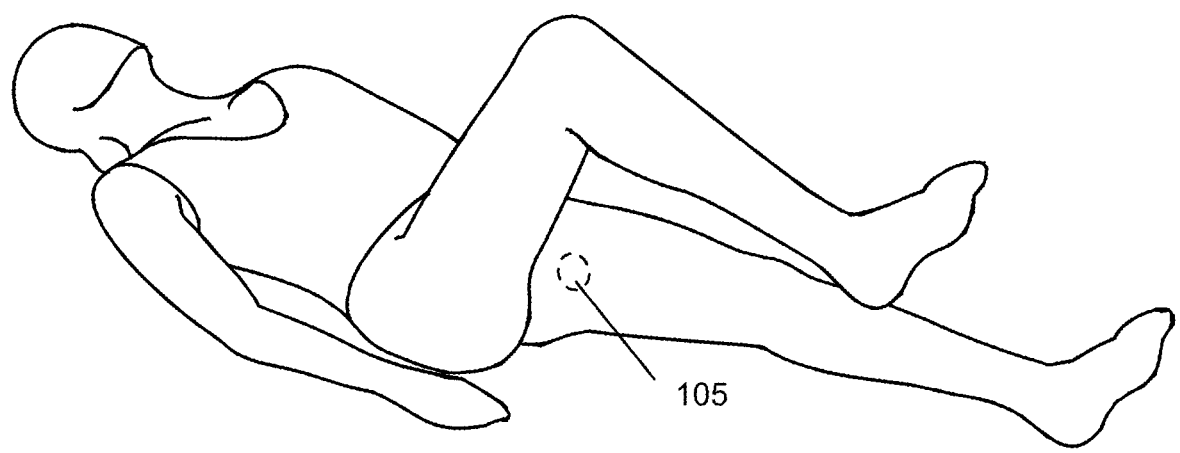
FIGURE 2C

SYSTEM AND METHOD FOR MONITORING CORE BODY TEMPERATURE

CROSS-REFERENCE TO RELATED APPLICATIONS

This application claims the benefit of U.S. Provisional Application Ser. No. 62/532,306, filed on 13 Jul. 2017, and U.S. Provisional Application Ser. No. 62/377,526 filed on 19 Aug. 2016, which are each incorporated herein in their entireties by this reference.

TECHNICAL FIELD

This invention relates generally to the wearable device field, and more specifically to an improved system and method for non-invasively monitoring core body temperature and related body status parameters.

BRIEF DESCRIPTION OF THE FIGURES

FIGS. 2A-2C depict variations of target user locations for an embodiment of a system for monitoring core body temperature;

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Overview

Figure 1A:
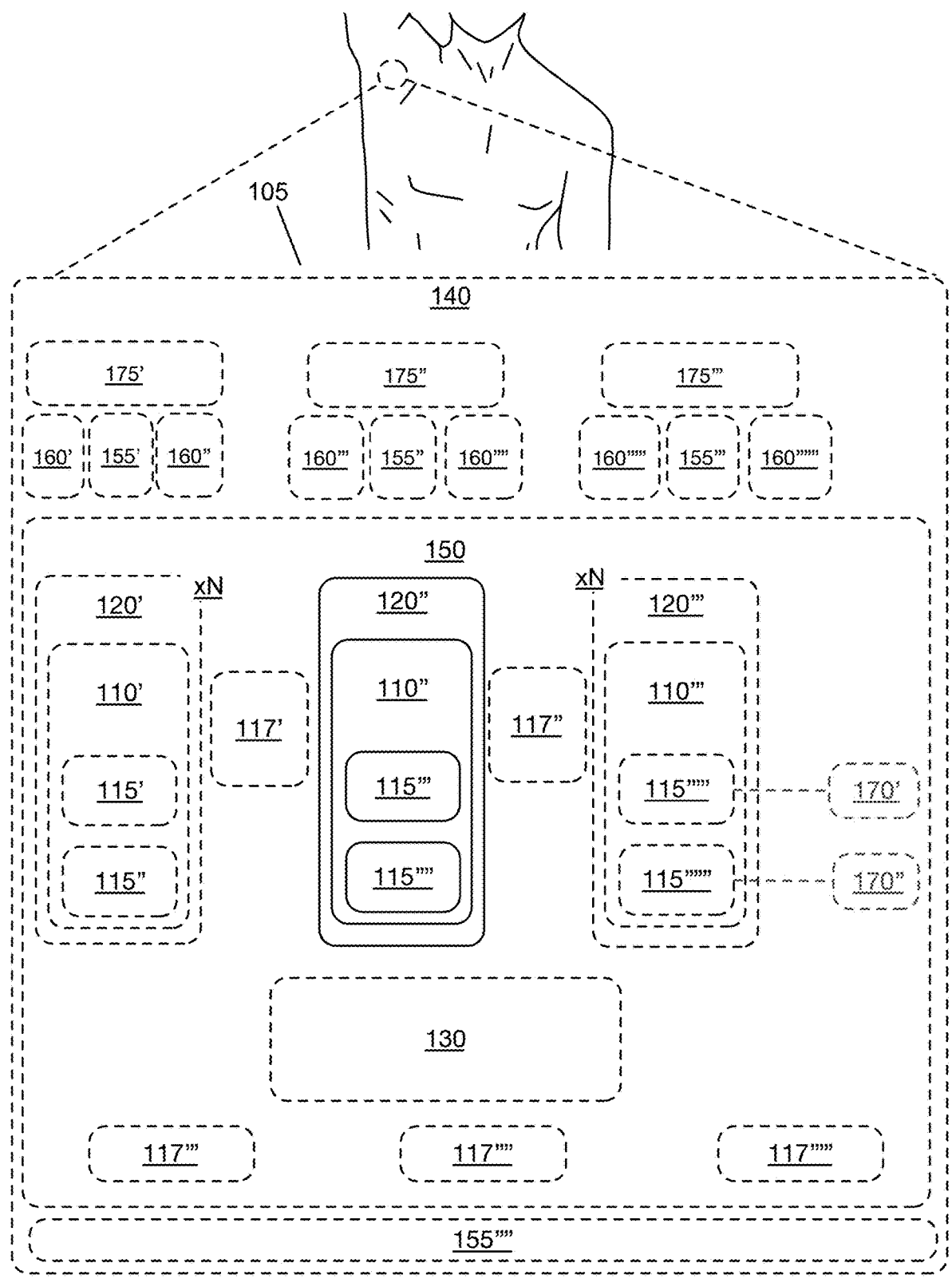
FIG. 1A-1B depict variations of embodiments of a system for monitoring core body temperature.
Figure 1B:
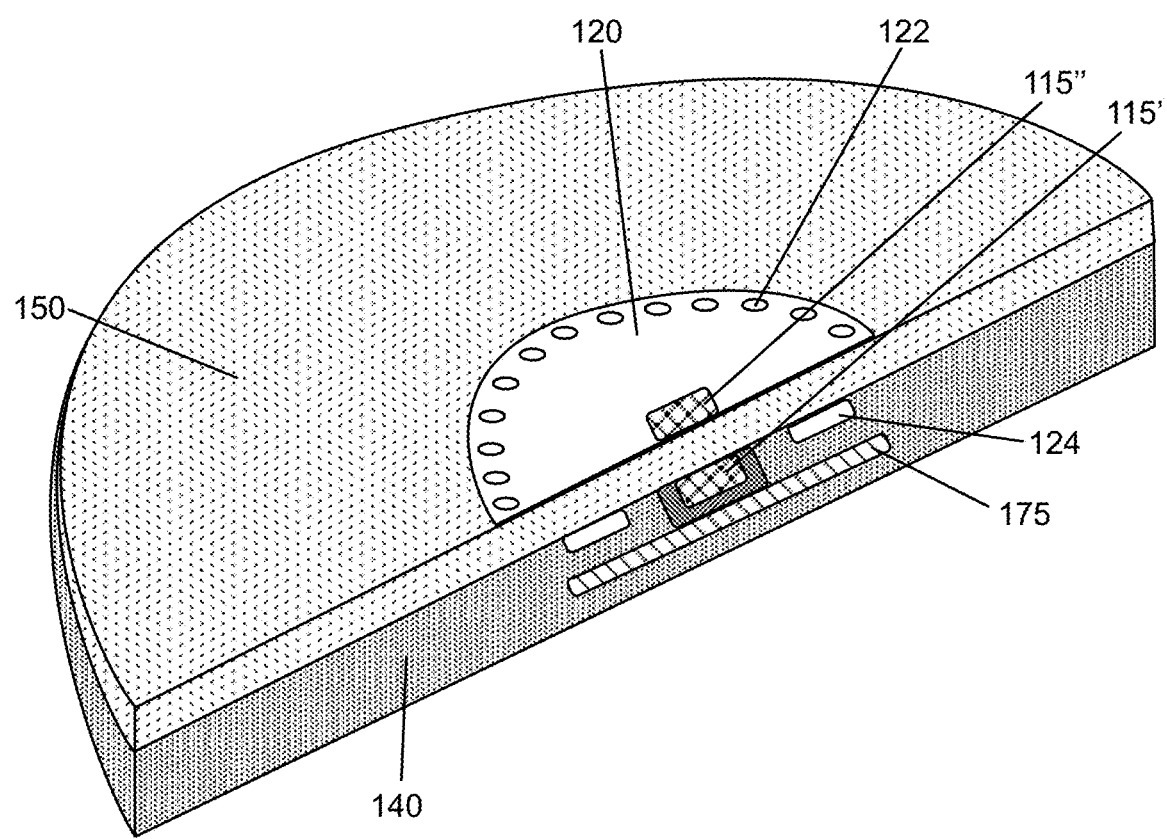

As shown in FIGS. 1A-1B, embodiments of a temperature monitoring device 105 (e.g., for monitoring core body temperature) can include: a heat flux channel 110, a first temperature sensor 115' thermally coupled to the heat flux channel 110, a second temperature sensor 115" thermally coupled to the heat flux channel 110, and a thermal cage 120 thermally coupled to the heat flux channel 110. The temperature monitoring device 105 can optionally include one or more supplemental sensors, a processing and control subsystem 130, substrates 150, thermal gap fillers 155, thermal insulation 160, a housing 140, cooling features 165 (e.g., convection fans, vents, etc.), heat sinks 170 (e.g., arranged proximal the edges of the substrate 150), and/or supplemental thermal features 180 (e.g., heat shields, thermal insulation layers, etc.). However, the temperature monitoring device 105 can include any suitable component for facilitating core body temperature monitoring.

In a variation, the system 100 can define a thermally conductive path extending away from a user-coupling surface of the system 100. In an example, the thermally conductive path can include: a housing segment (e.g., a user-facing region 144), a heat collector (e.g., magnet, an other thermally conductive heat collector, etc.), a thermally conductive filler 155, an inner temperature sensor 115', and a heat flux channel 110 thermally arranged in series from the user-coupling surface. The substrate 150 can additionally include a thermal cage 120, defined through the substrate thickness and arranged around the heat flux channel 110, where the thermal cage 120 can functions to prevent (and/or redistribute) lateral thermal leakage out of the heat flux channel 110 and/or prevent (and/or redistribute) thermal leakage into the heat flux channel 110. The system 100 can additionally include an outer temperature sensor 115", coupled to the thermal cage 120, that opposes the inner temperature sensor 115', where the inner and outer temperature sensors 115', 115", can be cooperatively used to determine the heat flux through the thermally conductive path. In another variation, the system 100 can include a multi-flux temperature monitoring device 105 including two or more heat flux channels 110 associated with two or more measurement sites (e.g., at different external skin regions of the user; at a non-organic material surface, such as for industrial applications; etc.). In an example, the temperature monitoring device 105 can include: a first and a second heat flux channel 110', 110", encapsulated by a housing 140 and each defining a length extending along an axis substantially perpendicular to the face of the housing 140, where the first heat flux channel 110' is associated with a first measurement site proximal a first region of the user-facing face of the housing 140, and where the second heat flux channel 110" is associated with a second measurement site proximal a second region of the user-facing face of the housing 140; a first set of temperature sensors 115 (e.g., including a first and a second temperature sensor, 115', 115", etc.) thermally coupled to the first heat flux channel 110' and operable to measure first temperature data indicative of first temperature change through the first heat flux channel 110' during a time period; a second set of temperature sensors 115 (e.g., including a third and a fourth temperature sensor, 115''', 115'''', etc.) thermally coupled to the second heat flux channel 110" and operable to measure second temperature data indicative of second temperature change through the second heat flux channel 110" during the time period; and a first and a second thermal cage 120', 120" respectfully thermally coupled to and respectfully arranged around the first and the second heat flux channels 110', 110" along the lengths of the first and the second heat flux channels 110', 110". In a specific example, the temperature monitoring device 105 can further include a third heat flux channel 100''' associated with a third measurement site; a third set of temperature sensors 115 (e.g., including a fifth and sixth temperature sensor, 115''''', 115'''''', etc.) thermally coupled to the third heat flux channel 110'''; and/or a third thermal cage 120' thermally coupled to the third heat flux channel 110''' (e.g., where a processing system can be operable to determine core body temperature measurements based on temperature data from the sets of temperature sensors 115; etc.). In a specific example, as shown in FIG. 1A, heat collectors 175', 175", 175''' (e.g., arranged between a user-facing region of the housing and respective temperature sensors of the heat flux channels; etc.) and thermal gap fillers 155', 155", 155''' can be associated with each heat flux channel (e.g., arranged between respective heat collectors respective temperature sensors of the heat flux channels; etc.). However, the system 100 can include any suitable number of heat flux channels 110 associated with (e.g., thermally coupled to) any suitable number of temperature sensors 115 and thermal cages 120, across any suitable number of temperature monitoring devices 105 and users.

The temperature monitoring device 105 functions to non-invasively monitor the core body temperature of a user, such as through non-invasively collecting user temperature measurements, where the user temperature measurements can be used in determining core body temperature over time (e.g., based on determination of one or more perfusion parameters) and/or other related body status parameters (e.g., vascularity or skin thickness, heat loss from the body, skin temperature, galvanic skin response, etc.) of the user. The temperature monitoring device 105 can additionally or alternatively function to generate one or more health status parameters (e.g., fever condition parameter, physiological status parameter, psychological status parameter, diagnostic analyses, treatment monitoring parameters, treatment response parameters, health recommendations, etc.) associated with user conditions based on user temperature measurements, determined core body temperatures and/or supplemental sensor data.

Embodiments of the system 10o and/or method 200 can be used for characterizing user conditions including a fever-associated condition, which can include one or more of: fever (e.g., continuous fever, intermittent fever, remittent fever, Pel-Ebstein fever, fevers with other suitable temperature patterns, etc.), infectious diseases (e.g., malaria, gastroenteritis, Lyme disease, infectious mononucleosis, Ebola, HIV infection, influenza, etc.), cancer (e.g., kidney cancer, leukemia, lymphomas, etc.), immunological diseases (e.g., inflammatory bowel diseases, lupus erythematosus, sarcoidosis, Kawasaki disease, Horton disease, granulomatosis with polyangiitis, Still disease, autoimmune hepatitis, relapsing polychondritis, etc.), immune reactions (e.g., incompatible blood products, incompatible organ products, etc.), skin conditions (e.g., boils, abscess, other skin inflammations, etc.), tissue destruction (e.g., associated with infarction, crush syndrome, hemolysis, surgery, rhabdomyolysis, cerebral bleeding, etc.), metabolic disorders (e.g., Fabry disease, gout, *porphyria*, etc.), and/or other suitable conditions related to fever. Additionally or alternatively, user conditions can include and/or be otherwise associated with: fertility (e.g., female health tracking, female cycle tracking, pregnancy planning, etc.), cardiovascular conditions (e.g., conditions related to blood pressure, vasodilation, vasoconstriction, vasocongestion, etc.), patient monitoring (e.g., in-home monitoring, monitoring in a hospital setting, continuous monitoring, etc.), sepsis, diseases affecting core temperature, treatment response evaluation (e.g., physiological response to treatments such as medication), disease research (e.g., using core temperature data to provide insights into causes, symptoms, and/or treatments for disease), ambulatory settings (e.g., ICU settings), sports medicine (e.g., athlete performance tracking, athlete health tracking), at-risk professions (e.g., astronauts, fire fighters, professionals at-risk of heat exhaustion and/or heat stroke, etc.), and/or other suitable conditions and/or applications.

As shown in FIGS. 1 and 2A-2C, the temperature monitoring device 105 of the system 100 is preferably configured to couple to a user at an axilla region of the user, but can additionally or alternatively be configured to couple to a user's forehead, sternum, inner thigh, a location proximal an artery of the user, and/or any suitable anatomical location in relation to the user. The temperature monitoring device 105 is preferably positioned on top of the skin of a user (e.g., as opposed to coupling the temperature monitoring device 105 to a subcutaneous region of the user through penetration of the skin or insertion into an orifice) at a location with vascularity, where core temperature is present relatively near the surface of the target site, but can otherwise be positioned.

Figure 3:
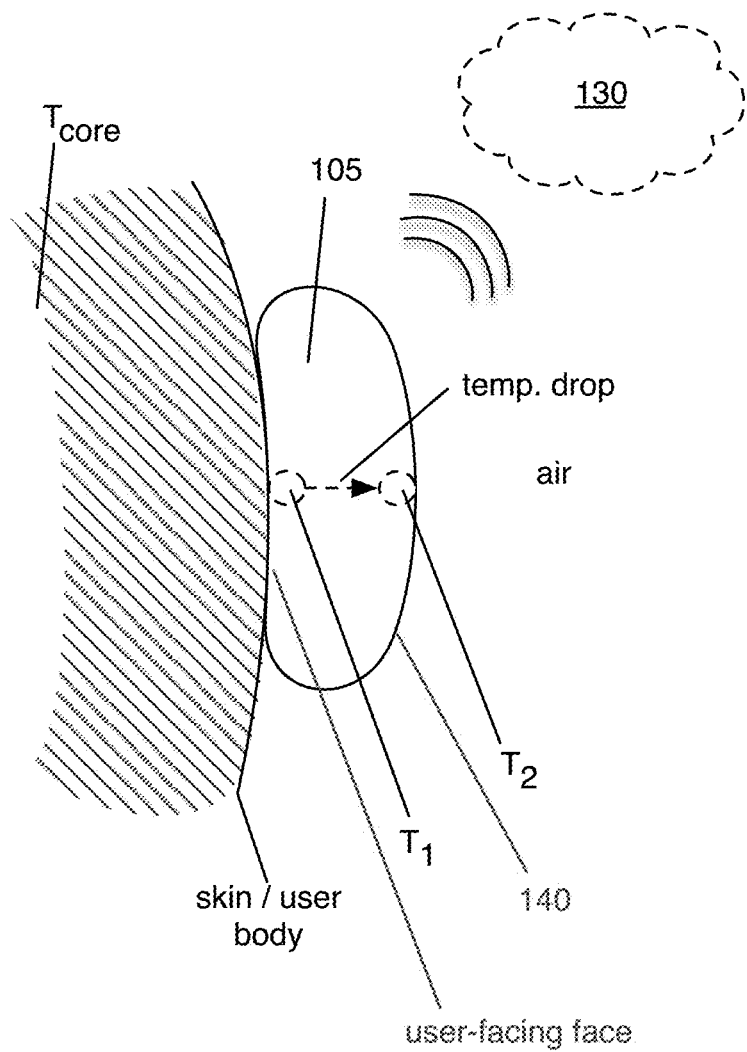
FIG. 3 depicts a schematic representation of heat flow in a variation of a system for monitoring core body temperature.

In an example of temperature monitoring device operation, a user can place the temperature monitoring device 105 onto a target skin surface at an axilla region of the user. The temperature monitoring device 105 can couple to the user through an adhesive positioned on an exterior housing surface of a user-facing region 144 of the housing 140. Heat from the temperature skin surface can be directed through a housing segment, a heat collector (e.g., a magnet protruding from the housing 140), a thermal gap filler 155 (e.g., arranged between the heat collector and a temperature sensor 115 of the heat flux channel 110; etc.), and into a heat flux channel no where temperature sensors 115 are arranged. One or more thermal cages 120 surrounding the one or more heat flux channels 110 can prevent environmental heat leakage into the heat flux channel 110 and lateral heat leakage out of the heat flux channel 110. As shown in FIG. 3, temperature sensors 115 positioned at beginning and end regions 112, 114 of the heat flux channels 110 can measure the temperature drops through the channels. Additional temperature sensors 115 arranged at different regions of the device can collect measurements used in accounting for heat gradients and/or cross-talk between heat flux channels 110. Collected temperature data can be stored for subsequent transmission (e.g., to a remote server, to a user device, etc.) and processing in order to determine a core body temperature and/or other body parameters of the user. However, the temperature monitoring device 105 can be otherwise configured for determining core body temperature.

The temperature monitoring device 105 can be used in embodiments of a system 100 and/or method 200 that functions to process collected temperature data to monitor user's core body temperature and/or related parameters over time (e.g., a series of temperature-associated parameters including a series of core body temperature measurements over time, normalized core body temperature measurements, core body temperature patterns, trends, combined core body temperature measurements determined from individual core body temperature measurements extracted from temperature data associated with different pairs of heat flux channels no, etc.). The system 100 can optionally include: a processing system (e.g., a remote processing system such as a server, at least one networked computing system, stateless, stateful; a local processing system, such as a desktop computing system; a mounting system configured to mount the temperature monitoring device 105; a processing and control subsystem of the temperature monitoring device; etc.), a user device (e.g., mobile computing device such as a smartphone, tablet, smart glasses, other computing devices, etc.), secondary wearable devices, a physician notification system, a substance regulation system (e.g., pill dispenser, IV dispenser, etc.), and/or any other suitable component. In an example, the temperature monitoring device 105 samples data (e.g., temperature data, etc.) indicative of a user's core body temperature while the temperature monitoring device 105 is connected to the user body and transmits the collected temperature data to a processing system (e.g., remote server, user device, etc.), where the processing system can process the temperature data into: representative core body temperature value(s) (e.g., for a monitoring session, for multiple time points within a single monitoring session); changes in the representative core body temperature value(s) over time (e.g., for intra- or inter-monitoring session values); and/or any other suitable derivatory data. In another example, the temperature monitoring device 105 can include a processing and control subsystem 130 operable to process the temperature data sampled at the temperature monitoring device 105 into core body temperature measurements (e.g., without leveraging the processing system of an additional device, etc.). The components of the system 100 can be physically and/or logically integrated in any manner, and any suitable components can perform any suitable portions of embodiments of a method 200 for characterizing core body temperature and/or other suitable physiological parameters at any suitable time and frequency in any suitable order, such as in relation to approaches described in U.S. Provisional Application Ser. No. 62/532,306, filed on 13 Jul. 2017, which is herein incorporated in its entirety by this reference. Additionally or alternatively, distribution of functionality across components of the system 100 can be configured in any suitable manner. However, the system 100 can include any suitable components configured in any suitable manner.

2. Benefits

The system 100 and/or method 200 can confer several benefits over conventional methodologies used for monitoring core body temperature. For example, conventional methodologies (e.g., rectal probes, one-time use ingestible pills) can be expensive, inconvenient, possess limited accuracy, and/or invasive. In specific examples, the system 100 and/or method 200 can confer one or more of the following:

First, the technology can include a core body temperature monitoring device that is non-invasive and consumer-friendly. For example, the core temperature monitoring device can operate on top of a user's skin, foregoing any need for penetration of the skin. In a second example, the core temperature monitoring device can couple to and monitor the user's core body temperature at a user exterior surface (e.g., skin; a non-orifice surface, such as an armpit, forehead, etc.), thereby negating or reducing the need for device insertion into a body orifice. Additionally or alternatively, the core temperature monitoring device can be lightweight and possess a small form factor, thereby facilitating an unobtrusive user experience when the monitoring device is coupled to the user's body (e.g., when the user is sleeping, when the user is moving, etc.). Data collected by the monitoring device can be transmitted wirelessly to a remote component (e.g., remote server, user device, etc.), which can circumvent the need for any exposed wiring from the monitoring device. The potential features described above can be provided while the exterior of the core temperature monitoring device is kept thermally cool, so as to not burn the user.

Second, the technology can enable substantially accurate core body temperature determination (e.g., within a predetermined range of error, such as within 5° C.) by employing multiple temperature sensors. In one variation, the system 100 can include two temperature sensors per heat flux channel, such that the system 100 can collect both user body temperature measurements and device temperature measurements, where the device temperature measurements can be used to correct for: heat gains from the device itself, heat losses to the ambient environment and lateral heat flux, and/or other heat gains or losses to and/or from the temperature sensor sampling the user body temperature measurement. The system 100 can further promote accurate temperature readings by controlling heat flux through the system 100. In one variation, heat flux through the system 100 is controlled by directing heat through one or more designated heat flux channels in the device, while preventing unwanted lateral heat flow radially outwards and preventing heat flow from the environment into the heat flux channels. Additionally or alternatively, the technology can produce substantially accurate measurements of body temperature changes over time (e.g., where the measured body temperatures can be inaccurate, but the temperature changes can be substantially accurate).

Third, heat flow-controlling components of the monitoring device can provide thermal insulation for heat-sensitive components of the device (e.g., processing modules, communication modules, charging elements, power modules, etc.), thereby enabling increased durability and a longer life-span of the device.

The technology can, however, provide any other suitable benefit(s) in the context of core body temperature and/or related body parameter monitoring.

3. System

As shown in FIGS. 1A-1B, a temperature monitoring device 105 includes: a heat flux channel 110, a first temperature sensor 115' thermally coupled to the heat flux channel no, a second temperature sensor 115" thermally coupled to the heat flux channel no, and a thermal cage 120 thermally coupled to the heat flux channel no. The temperature monitoring device 105 can optionally include one or more supplemental sensors, a processing and control subsystem 130, heat collectors, substrates 150, thermal gap fillers 155, thermal insulators, a housing 140, and/or other suitable components.

3.1 Heat Flux Channel

Figure 6A:
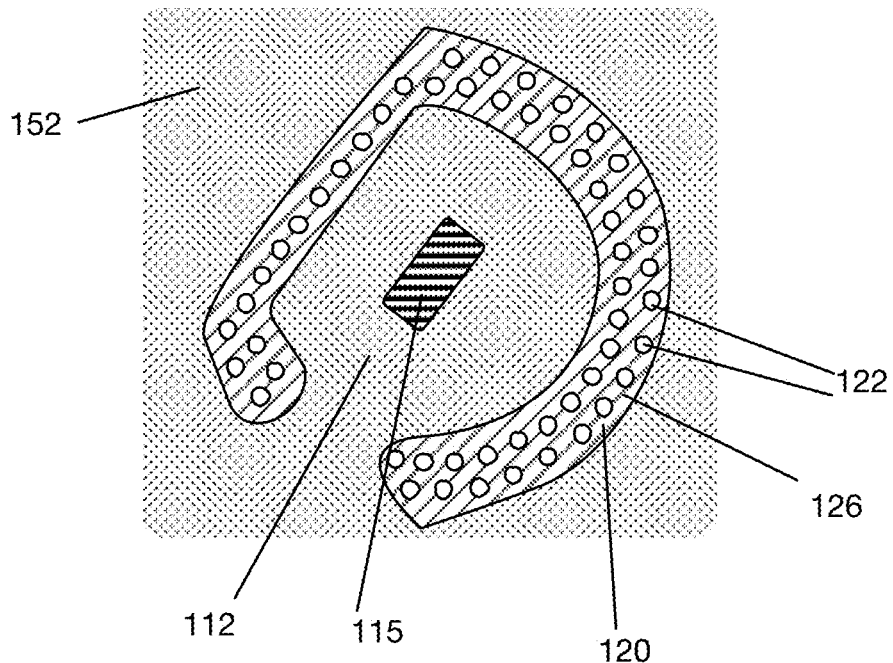
FIGS. 6A-6B depict variations of an inner substrate layer and an outer substrate layer in an embodiment of a system for monitoring core body temperature.
Figure 6B:
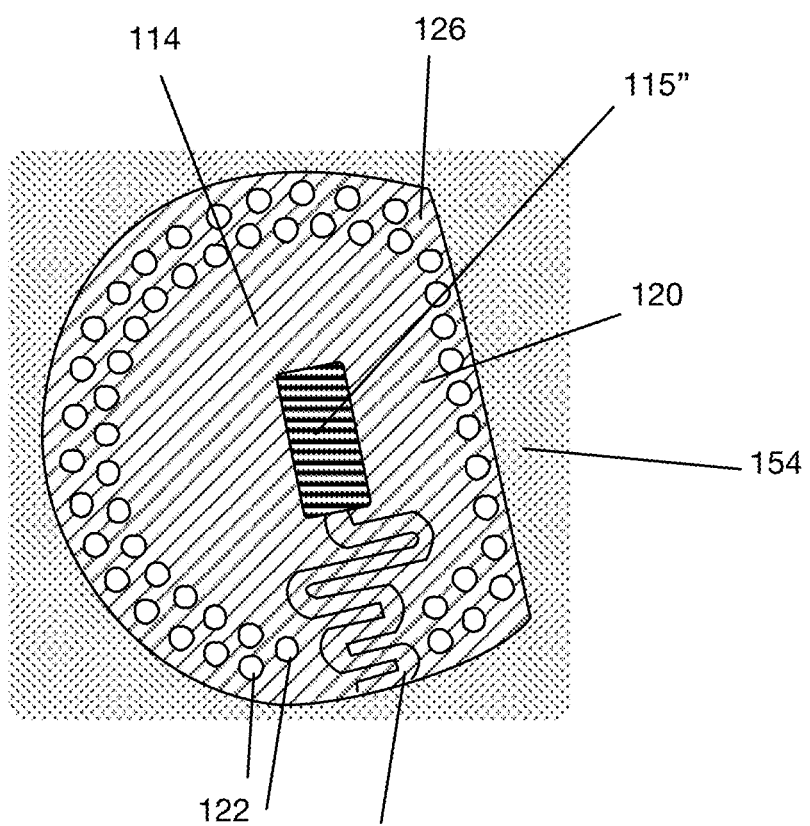

As shown in FIGS. 1 and 6A-6B, the temperature monitoring device 105 can include a heat flux channel 110, where a heat flux channel no functions to direct heat through a thermal path defining regions for recording temperature measurements to be used in determining core body temperature.

The heat flux channel no preferably extends along a thickness of the temperature monitoring device 105 (e.g., along an axis substantially perpendicular to a target skin surface upon which the temperature monitoring device 105 is placed). In a first embodiment, the heat flux channel no is defined by the substrate 150. In one variation of the first embodiment, the heat flux channel no extends through the entirety of the substrate thickness. In a second variation, the heat flux channel no extends through a portion of the substrate thickness. In one example of the second variation, the heat flux channel no extends from the interior substrate surface toward the exterior substrate surface. In a second example of the second variation, the heat flux channel 110 extends from the interior substrate surface toward an orthogonal substrate surface. However, the heat flux channel no can be otherwise arranged relative to the substrate 150. Additionally or alternatively, one or more heat flux channels no can extend along any dimension of one or more suitable components. In a second embodiment, as shown in FIG. 4B, a heat flux channel no can be defined by multiple components (e.g., by the heat collector and substrate 150, etc.). For example, the heat flux channel no can be defined by and extend along a thickness of a heat collector and a thermal gap filler 155 situated between an interior housing surface and a substrate 150. In a second example, the heat flux channel 110 can be defined by a thermally conductive rod or channel, having a known thermal resistance, that extends through the device interior. However, heat flux channels no can be distinct from other components of the temperature monitoring device 105. Further, parameters of the heat flux channel no (e.g., width, height, thermal resistance, cross-section, length, etc.) can be tailored (e.g., minimizing lateral heat leakage, maximizing heat flux through the heat flux channel 110, etc.) based on the intended medical application, to meet a target thermal resistance, and/or otherwise adjusted based on any other suitable factor. However, heat flux channels 110 can be oriented in any suitable manner at any suitable location.

In a variation, two or more heat flux channels no of a temperature monitoring device 105 can be associated with the same or substantially similar channel thermal resistances, and/or the same or substantially similar couplings to the processing system (e.g., to the backend of the temperature monitoring device; to an ambient environment; to a processing and control subsystem; to other components of the temperature monitoring device; etc.) and/or to other suitable components. In another variation, two or more heat flux channels no of a temperature monitoring device 105 can be associated with varying channel thermal resistances and/or varying couplings to the processing system and/or to other suitable components. In an example, the system 100 can include a first, second, and third heat flux channel 110', 110", 110''' associated with a set of varying channel thermal resistances and a set of varying couplings to the processing system (e.g., where determination of the core body temperature for the time periods can be based on the set of varying couplings, the set of varying channel thermal resistances, and temperature data from sets of temperature sensors 115 associated with the heat flux channels 110, etc.). Additionally or alternatively, heat flux channels 110 and/or other suitable components can be configured to interact with the sample in different manners while optimizing certain parameters (e.g., without minimizing the reading values beyond a threshold amount; without incurring dominant lateral leakage effects or parasitics; etc.), where the differentiated interactions with the sample can facilitate signals suitable for accurately determining core body temperature In specific examples, a temperature monitoring device 105 can 1) include varying channel thermal resistances with identical coupling to the back (e.g., environment-facing region of the housing 140; end region 114 of a heat flux channel 110; outer layer of the substrate 150 of the device; etc.) 2) having identical channels with varying coupling to the back of the device and 3) a combination of 1) and 2) with varying channel thermal resistances combined with suitable varying coupling to the back of the device. In an example, variability across heat flux channels 110, measurement sites, and/or other suitable components can be facilitated by thermal coupling to one or more thermal features. In a specific example, the system 100 can include a first heat sink 170' (e.g., a large heat sink) thermally coupled to an end temperature sensor 115 (e.g., arranged proximal the end region 114 of a first heat flux channel 110', etc.) of a first set of temperature sensors 115 (e.g., corresponding to the first heat flux channel 110'), where the heat sink 170 is associated with a first coupling of the first heat flux channel 110' to the processing system, and where a second heat sink 170" (e.g., a small heat sink, etc.) can be thermally coupled to an end temperature sensor 115 of a second set of temperature sensors 115, and/or can be otherwise omitted. However, heat flux channels 110 and/or other suitable components can be associated with any suitable resistances, couplings, and/or other parameters that are different, substantially similar, and or the same across components.

Figure 8:
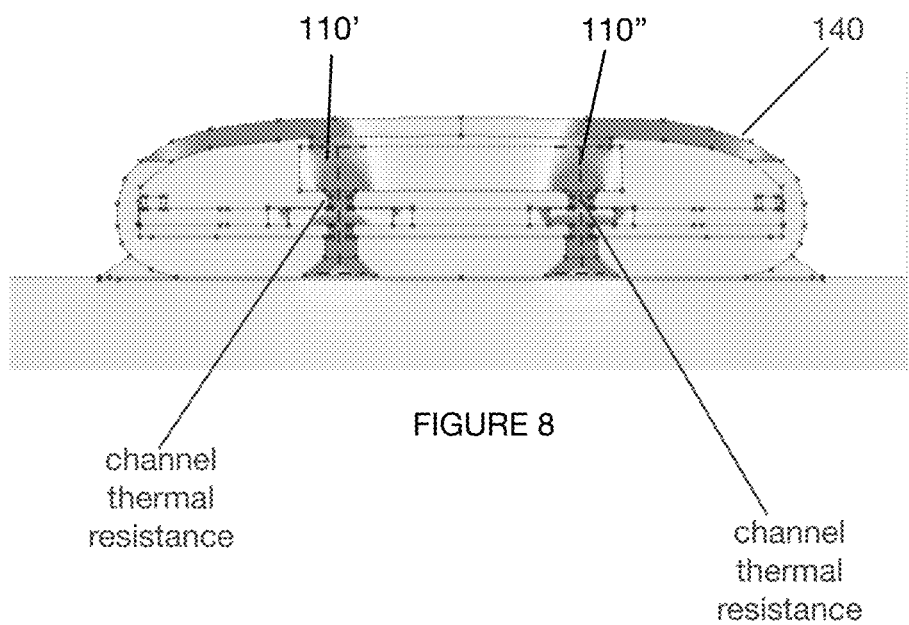
FIG. 8 depicts a schematic representation of a dual heat flux channel variation of a system for monitoring core body temperature.

A heat flux channel 110 preferably defines a beginning region 112 (e.g., proximal a measurement site) and an end region 114. A heat flux channel 110 is preferably associated with one or more measurement sites (e.g., an external region of the user at which the heat flux channel 110 is thermally interfacing; a target sample site; etc.). Heat is preferably directed from the beginning region 112 (e.g., where the heat originates from the measurement site, etc.) to the end region 114 (e.g., in a direction towards cooler regions of the heat flux channel no), but can additionally or alternatively be directed towards any suitable regions. Heat flux channels 110 can define substantially straight heat paths from the beginning to end regions 112, 114 of the heat flux channel 110, curved paths, angled paths, divergent paths, expanding paths, constricting paths, and/or any suitable heat paths. In a variation where the heat flux channel 110 extends along the substrate 150, a beginning region 112 can be proximal an inner layer of the substrate 150 (e.g., proximal a housing surface coupled to the user when the temperature monitoring device 105 is arranged on the user's skin), and the end region 114 can be proximal an outer layer of the substrate 150. In a specific example of this variation, the heat flux channel 110 is coextensive with layers of the substrate 150, such that the inner layer and outer layer of the substrate 150 respectively define a first and second end of the heat flux channel 110. However, the heat flux channel no can define any suitable regions. As shown in FIG. 8, the temperature monitoring device 105 can include a plurality of heat flux channels no (e.g., a dual-flux system), but can alternatively include only one heat flux channel no.

The heat flux channel no is preferably constructed with materials possessing a low thermal heat capacity (e.g., FR-4 material), but any portion of the heat flux channel no can be constructed using materials with any suitable thermal properties (e.g., thermally conductive, thermally insulative, etc.). In a first variation, the heat flux channel no can be constructed of substrate materials (e.g., when the heat flux channel no is arranged at the substrate 150. In a second variation, the heat flux channel no can be constructed of substrate materials and thermally conductive materials (e.g., metals, etc.). For example, a heat flux channel beginning region 112 can be constructed with substrate materials, and a heat flux channel end region 114 can be constructed with thermally conductive materials (e.g., copper). In another example, the heat flux channel 110 can include an inner and an outer concentric layer extending along a thermal path of the heat flux channel no. The inner and outer concentric layers can be respectively constructed with substrate 150 and thermally conductive materials. In a third variation, the heat flux channel no can be exclusively made of thermally conductive material. For example, a heat flux channel 110 can include a thermally conductive tube extending along a thermal path of the heat flux channel no. However, any portion of a heat flux channel 110 can be constructed using any suitable materials.

In a variation, the temperature monitoring device 105 can include a first and a second heat flux channel 110', no". The first heat flux channel 110' is preferably thermally insulated from the second heat flux channel no". For example, the first and second heat flux channels 110', 110" can be separated by thermally insulating material (e.g., substrate material, air gaps, vias 122, etc.). Additionally or alternatively, the heat flux channels no can be thermally coupled and/or have any suitable thermal relationship.

Figure 5A:
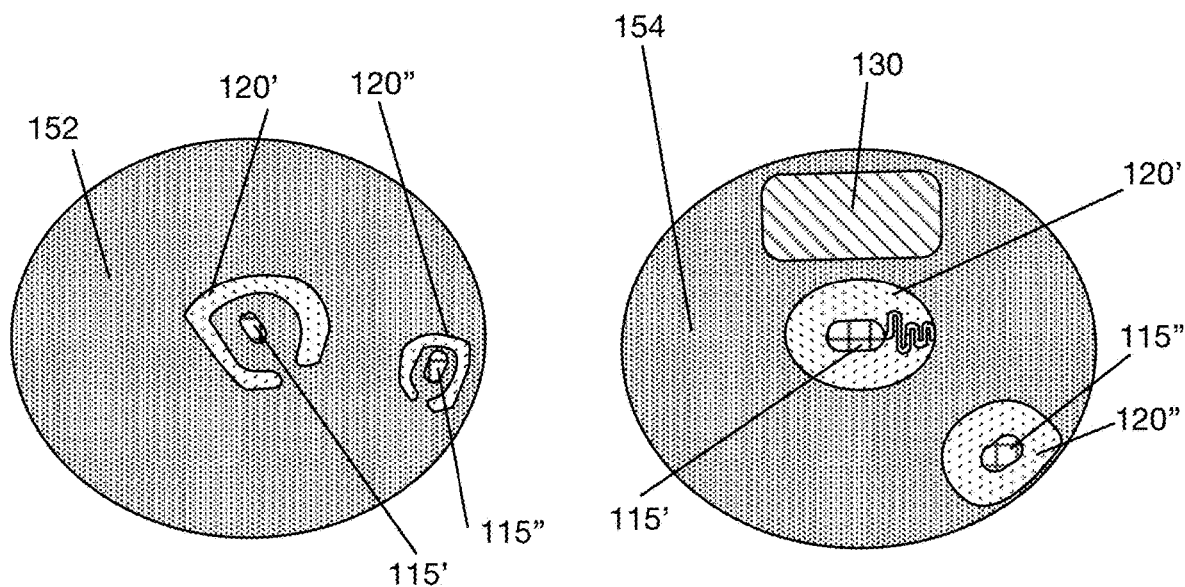
FIGS. 5A-5B depicts variations of a thermal cage in an embodiment of a system for monitoring core body temperature.
Figure 5B:
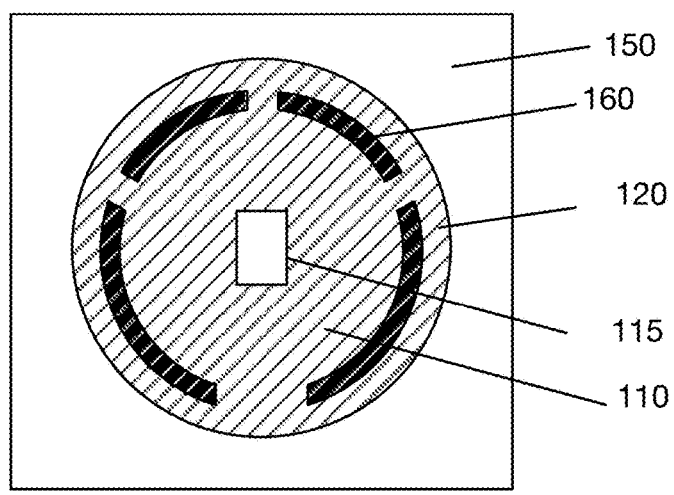

As shown in FIG. 5A, in a first specific example of this variation, the temperature monitoring device 105 can include a first heat flux channel 110' arranged proximal a central region of the substrate 150 (e.g., distant the perimeter of the substrate 150, and a second heat flux channel 110" proximal an edge of the substrate 150 (e.g., proximal a perimeter of the substrate 150. In this specific example, the first and second heat flux channels 110', 110" can be aligned along a radial axis of the substrate 150. The second heat flux channel 110" can be proximal a substrate edge that is distant from heat-sensitive and/or heat-generating components (e.g., a processing module, a power module, communications module, etc.).

In a second specific example of this variation, the first and second heat flux channels 110', 110" can both be proximal the central region of the substrate 150. In this specific example, the heat flux channels no can be aligned along a lateral and/or longitudinal axis). However, a heat flux channel no can be configured in any suitable fashion relative another heat flux channel no (e.g., distance of separation between heat flux channels 110, alignment, overlapping channels, non-overlapping channels, etc.).

However, heat flux channels 110 can be configured in any suitable fashion.

3.2 Temperature Sensor

As shown in FIGS. 1A-1B, the system 100 can include one or more temperature sensors 115 that function to measure temperature changes through one or more heat flux channels 110. The temperature sensors 115 can additionally or alternatively function to collect temperature measurements for reducing noise, evaluating heat gradients, determining target location parameters (e.g., vascularity, skin depth, skin resistance, etc.), and/or for any other suitable purpose.

The temperature monitoring device 105 preferably includes a pair of temperature sensors 115', 115" for each heat flux channel 110, but can alternatively include any suitable number of temperature sensors 115 for a given heat flux channel 110. Each pair of temperature sensors 115', 115", are preferably thermally coupled to the corresponding heat flux channel 110, but can be optionally thermally coupled to any suitable number of heat flux channels 110. For a given heat flux channel 110, temperature sensors 115 can be arranged within, adjacent, proximal, and/or otherwise positioned in relation to the regions (e.g., beginning, middle, end, etc.) of the heat flux channel 110. In a variation, a first temperature sensor 115' is arranged at the heat flux channel beginning region 112 (e.g., at a radial center of the beginning region 112), and a second temperature sensor 115" is arranged at the heat flux channel end region 114 (e.g., at a radial center of the end region 114). In this variation, the first temperature sensor 115' can be configured to measure a temperature at the location of device coupling to the user (e.g., a temperature at the target skin surface of the user), and the second temperature sensor 115" can be configured to measure heat that has flowed through the channel. In examples with temperature sensors 115 arranged at a heat flux channel end region 114 constructed with a different material (e.g., copper) than materials of the beginning region 112 and/or middle region (e.g., FR-4), the temperature sensor 115 can physically touch only the end region material, be physically situated at the interface between the end and middle regions such that the temperature sensor 115 is physically touching both the end and middle region materials (e.g., both copper and FR-4), and/or be otherwise positioned relative the heat flux channel end region 114. However, temperature sensors 115 associated with a heat flux channel 110 can be otherwise configured.

Additionally or alternatively, temperature sensors 115 can be placed at: intermediary regions between heat flux channels 110 (e.g., a temperature sensor 115 configured to collect temperature measurements indicating cross-talk between heat flux channels no), inner or outer layers of a substrate 150, arcuate regions around a substrate 150 (e.g., temperature sensors 115 configured to collect temperature measurements indicating heat gradients across the device), and/or at any suitable location in relation to the substrate 150 or other components of the temperature monitoring device 105.

As shown in FIG. 1A, in a specific example, the temperature monitoring device 105 can include eight temperature sensors: two sensors each for two heat flux channels 110 (e.g., where a sensor pair is configured to measure a temperature drop from the beginning region 112 to end region 114 of the respective heat flux channel 110), a supplemental temperature sensor 117' (and/or additional supplemental temperature sensors 117") positioned at a substrate region between the two heat flux channels 110 (e.g., configured to measure cross-talk between the heat flux channels 110), and three supplemental temperature sensors 117''', 117'''', 117''''' positioned arcuately around the circumference of the substrate 150 (e.g., configured to measure a heat gradient across the device). However, temperature sensors 115 can be otherwise located.

Types of temperature sensors 115 used in the temperature monitoring device 105 preferably include one or more thermistors (e.g., NTC thermistor, PTC thermistor), but can additionally or alternatively include a resistance temperature detector (RTD), a thermocouple, a semiconductor-based sensor, a heat flux sensor (e.g., thermopiles, Gardon gauges, Schmidt-Boelter gauges, etc.), and/or any other suitable type of temperature sensor 115. In an example, a heat flux channel can be thermally coupled to a beginning region temperature sensor (e.g., proximal a beginning region of a heat flux channel) and a heat flux sensor, where a temperature at an end region of the heat flux channel can be calculated from measurements from the sensors.

In a variation, one or more temperature sensors 115 can be electrically connected to other components (e.g., processing and control subsystem 130) through electrical traces 190 (e.g., substrate traces, thermal cage traces) etched onto the substrate 150 and/or components associated with the substrate 150. Traces 190 associated with temperature sensors 115 can have any suitable pattern, including a boustrophedon (e.g., as shown in FIG. 6B), serpentine, spiral, straight, curved, and/or any suitable pattern. In examples where a trace 190 defines a boustrophedon pattern, the boustrophedon arms can increase in length as the trace 190 becomes more proximal to a temperature sensor 115. However, the boustrophedon pattern can possess any suitable feature (e.g., arms of equal length, arms increasing in thickness, etc.). In examples where temperature sensors 115 are positioned within a heat flux channel 110 encapsulated by a thermal cage 120, the temperature sensors 115 are preferably electrically connected to traces 190 exiting the heat flux channel 110 through a break in the thermal cage 120 (e.g., as shown in FIG. 6A). In a specific example, a temperature sensor 115 arranged at an end region 114 of a heat flux channel 110 is electrically connected to a copper trace 190 defining a boustrophedon pattern. However, electrical connectors associated with the temperature monitoring device 105 can be configured in any suitable fashion.

3.3 Thermal Cage

As shown in FIGS. 5A and 6A-6B, the temperature monitoring device 105 can include a thermal cage 120, which functions to minimize lateral heat leakage from the temperature monitoring device 105 (e.g., heat leakage substantially perpendicular a layer axis through layers of a substrate 150, substantially perpendicular an axis along the heat flux channel thermal path, etc.) by thermally insulating and/or thermally redirecting lateral heat flow towards the intended end-region of the heat flux channel 110. The thermal cage 120 can include one or more thermal insulation features (e.g., vias 122, insulating cuts, air pockets 124, etc.), thermal spreaders 126, and/or any other suitable component possessing any appropriate thermal properties. The temperature monitoring device 105, substrate 150, and/or heat flux channel 110 can include one or more thermal cages 120.

The thermal cage 120 is preferably thermally connected to the heat flux channel no, but can be otherwise related to the heat flux channel no. Each thermal cage 120 is preferably associated with a single flux channel, but can alternatively be associated with multiple flux channels. The thermal cage 120 can thermally insulate the heat flux channel no (e.g., from the remainder of the substrate 150, from the ambient environment, etc.), thermally connect the heat flux channel no to a thermal endpoint (e.g., ambient environment, housing 140, heat source, etc.), and/or be otherwise connected to the heat flux channel no. The thermal cage 120 can additionally distribute heat across the heat flux channel cross-section (e.g., along the channel length, across the channel length), and/or otherwise distribute heat across the heat flux channel no.

The thermal cage 120 preferably entirely or partially encloses one or more heat flux channels no. The thermal cage 120 can enclose the heat flux channel no along all or a portion of the heat flux channel's: length, arcuate segment, and/or any other suitable portion of the heat flux channel no. In a first variation, the thermal cage 120 entirely encloses the heat flux channel no along a heat flux channel perimeter, except for a gap through which a temperature sensor trace 190 extends. The temperature sensor trace 190 can be electrically insulated (e.g., isolated) from the thermal cage 120 by a substrate material, electrical insulation (e.g., epoxy), and/or any other suitable material. In a second variation, the thermal cage 120 defines the heat flux channel perimeter. In this variation, the thermal cage 120 can be physically contiguous with the heat flux channel 110. For example, as shown in FIG. 6B, an end region 114 of the heat flux channel 110 can be physically contiguous with a thermal cage 120 substantially encapsulating the heat flux channel 110. In a third variation, the heat flux channel 110 is separated from the thermal cage 120 by thermal insulation 160. In a fourth variation, the heat flux channel 110 is separated from the thermal cage 120 by thermally conductive material (e.g., a substrate segment, metal, etc.). However, the thermal cage 120 can be otherwise arranged relative to the respective heat flux channel 110. However, the thermal cage 120 can be otherwise constructed.

The thermal cage 120 preferably entirely or partially encloses one or more temperature sensors 115. For example, as shown in FIGS. 6A-6B, the thermal cage 120 can substantially arcuately enclose a temperature sensor 115 arranged at a heat flux channel 110. Additionally or alternatively, the thermal cage 120 can entirely or partially enclose any suitable component. However, the thermal cage 120 can have any suitable positional relationship relative other components of the system 100 (e.g., mounted to an interior surface of a housing 140, arranged within a thermal gap filler 155, etc.), and can be positioned at any suitable location.

As shown in FIG. 6A, a thermal cage cross-sectional profile can substantially possess an annular ring shape and/or any suitable shape. In a variation where the cross-sectional profile is ring-shaped, the ring can include a break in the ring, but can alternatively define a fully formed ring without any breaks. Breaks in the ring can provide a path for electrical connections (e.g., electrical connections between a thermal cage-encapsulated temperature sensor 115 and a processing and control subsystem 130 outside the thermal cage 120). The thermal cage 120 can extend any suitable distance along an axis parallel a thermal path of a heat flux channel 110 (e.g., a heat flux channel 110 thermally coupled to the thermal cage 120), but can additionally or alternatively extend along a substrate thickness, a temperature monitoring device thickness, and/or at any suitable angle relative any suitable reference feature. However, the thermal cage 120 can define any suitable volume, shape, dimensions, and/or geometric property.

The thermal cage 120 can optionally define an interior surface and an exterior surface. In a variation, the interior surface can define a heat flux channel 110. In this variation, the exterior surface can be physically contiguous with region of the substrate 150 distinct from the heat flux channel 110. However, surfaces of the thermal cage 120 can be otherwise positioned. The interior and exterior surfaces can be constructed with different materials. For example, an interior surface can be constructed with thermally conductive materials, and an exterior surface can be constructed with thermally insulative materials. Alternatively, the interior and exterior surfaces can be constructed with the same materials, but any portion of the thermal cage 120 can be constructed using any suitable materials. However, the thermal cage 120 can define any suitable surfaces and/or reference features possessing any suitable properties.

The thermal cage 120 can be grounded to minimize electromagnetic interference (EMI) with other components (e.g., a communications module), but the temperature monitoring device 105 can additionally or alternatively include any suitable mechanism (e.g., electromagnetic shielding, EMI filters, snubber network, etc.) for preventing EMI.

3.3.A Thermal Cage—Thermal Features

In variations, the thermal cage 120 can include one or more thermal features, which function to minimize lateral heat leakage out of the heat flux channel 110 and/or minimize ambient heat leakage into the heat flux channel 110. Thermal features can include any combination of vertical interconnect accesses (e.g., vias 122), insulating cuts (e.g., an insulating air pocket 124), thermally insulating shields, and/or other suitable thermal mechanisms. The thermal features preferably extend through all or part of the substrate thickness, but can alternatively be otherwise arranged. The thermal features are preferably arranged proximal, more preferably contiguous with but alternatively separate from, the heat flux channel 110, but can alternatively be otherwise arranged.

3.3.B Thermal Cage—Vias

In a variation where the thermal cage 120 includes one or more vias 122, the vias 122 can be blind vias (e.g., exposed only on a single side of a substrate 150, buried vias (e.g., unexposed on sides of the substrate 150, thermal vias (e.g., for redirecting heat), and/or vias 122 of any suitable type. In an example, the thermal cage 120 can include a set of thermally conductive vias 122 thermally coupling the first temperature sensor 115' to the second temperature sensor 115" (e.g., facilitating heat travel from a first temperature sensor to a second temperature sensor by minimizing lateral heat leakage as heat travels through a heat flux channel from the first temperature sensor to the second temperature sensor; etc.), where the set of thermally conductive vias 122 extend along the length of the heat flux channel 110 from a beginning region 112 to an end region 114 of the heat flux channel 110. Vias 122 are preferably embedded within the thermal cage 120, but can additionally or alternately be partially arranged within the thermal cage 120, attached to the exterior of the thermal cage 120, cooperatively define a thermal cage exterior, and/or positioned at any suitable location relative the thermal cage 120. Relative other vias 122, a via 122 can be adjacent, distant, proximal, thermally connected and/or be otherwise positioned.

Figure 7:
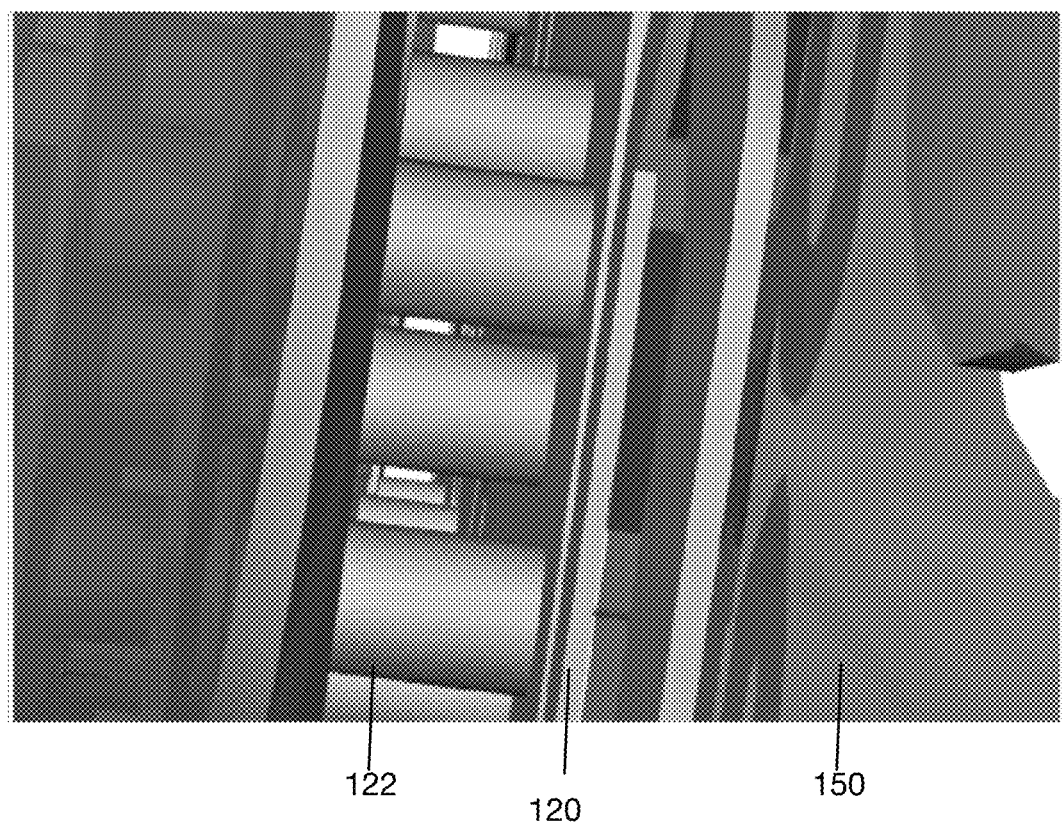
FIG. 7 depicts an internal view of a variation of a thermal cage and substrate in an embodiment of a system for monitoring core body temperature.

As shown in FIG. 7, each via 122 preferably defines a tubular shape, but can otherwise define any suitable shape. Vias 122 can extend any suitable distance along the depth of the thermal cage 120, but can additionally or alternatively have any suitable dimensions. Vias 122 can define an interior and exterior region (e.g., an interior lumen of a via tube and an exterior region defining the interior lumen). Exterior regions of a via 122 are preferably constructed using thermally conductive materials (e.g., metals such as copper), but can alternatively be thermally insulative. Interior regions of a via 122 (e.g., the via lumens) are preferably filled with thermally conductive material, but can alternatively be hollow (e.g., air filled), filled with thermal insulation 160 and/or with any other suitable material. However, portions of a via 122 can be constructed with any suitable materials.

In a variation, the thermal cage 120 can include a first and a second set of vias 122. The first and second set of vias 122 can include an equal number of vias 122, such that each via 122 of the first set of vias 122 can be uniquely paired with a via 122 of the second set of vias 122 (e.g., a second set via 122 positioned radially outwards from a first set via 122) in a 1:1 relationship, but can alternatively include an unequal number of vias 122. The first and second set of vias 122 can be positioned in any suitable configuration. For example, as shown in FIGS. 6A-6B, each set of vias 122 can include vias 122 at arcuate positions spaced around a perimeter of the thermal cage 120. As shown in FIG. 6B, in a specific example, the first set of vias 122 is arranged radially inwards from the second set of vias 122. In other examples, as shown in FIGS. 6A-6B, vias 122 can be arranged at positions forming a line segment and/or any other suitable geometric form and/or shape. However, the thermal cage 120 can include any number of vias 122 in any suitable configuration. Various types of vias 122 can be used in one solution. In one example, an outer set of vias 122 can be constructed of thermally insulative materials, and an inner set of vias 122 can be constructed of thermally conductive materials. However, various via types can be arranged in any suitable configuration.

3.3.C Thermal Cage—Thermal Spreader

The thermal cage 120 can optionally include a thermal spreader 126, which functions to spread heat across portions of the thermal cage 120. A thermal spreader 126 can additionally or alternatively function to minimize heat gradients across regions proximal a temperature sensor 115.

A thermal spreader 126 is preferably thermally coupled to one or more heat flux channels 110. In an example, as shown in FIGS. 6A-6B, a thermal spreader 126 can be physically contiguous with a heat flux channel 110. Additionally or alternatively, a thermal spreader 126 can be thermally coupled to a thermal insulating feature, a temperature sensor 115, a substrate 150, and/or any suitable component. As shown in FIGS. 6A-6B, in an example, a thermal spreader 126 is thermally coupled to one or more vias 122 of the thermal cage 120. The thermal spreader 126 is preferably physically contiguous with the one or more vias 122, but can alternatively be thermally connected by a thermal manifold and/or otherwise connected to the vias 122. For example, a thermal spreader 126 can define and/or thermally encapsulate an end of a via 122. In another example, a via 122 can extend through a thermal spreader 126. Additionally or alternatively, the thermal spreader 126 can be adjacent, proximal, and/or physically distant from one or more vias 122, but a thermal spreader 126 can otherwise be configured relative to a via 122. In another example, a thermal spreader 126 is thermally coupled with an insulating cut. For example, an insulating cut (e.g., air gap) can be arranged within, adjacent to, and/or proximal to a thermal spreader 126, but can otherwise be configured.

A thermal spreader 126 is preferably arranged proximal a beginning and/or end region 114 of the heat flux channel 110, but can additionally or alternatively be positioned proximal any suitable portion of the heat flux channel 110 and/or temperature monitoring device 105. In an example, the thermal spreader 126 can be arranged at a thermal spreader 126 arranged at the end region 114 of the heat flux channel 110, where the thermal spreader 126 is physically and thermally coupled to the set of thermally conductive vias 122 and an end temperature sensor 115 arranged at an end region 114 of the heat flux channel 110. The thermal spreader 126 can have any suitable depth. For example, a thermal spreader 126 can substantially encapsulate a heat flux channel beginning region 112, but not encapsulate a heat flux channel middle region and end region 114. The thermal spreader 126 can additionally have any suitable width. For example, a thermal spreader 126 can extend along the entire width of a substrate 150. However, the thermal spreader 126 can have any suitable dimensions and be arranged at any suitable location of the thermal cage 120.

The thermal spreader 126 is preferably constructed from thermally conductive materials (e.g., metals such as copper), but can additionally or alternatively be constructed with any suitable material possessing any suitable thermal properties (e.g., specific heat capacity, insulation thickness, density, surface emissivity, thermal bridging, etc.).

A thermal cage 120 can include any number of thermal spreaders 126. As shown in FIGS. 6A-6B, in an example, a thermal cage 120 includes a first and a second thermal spreader 126', 126". The first and second thermal spreaders 126', 126" can be arranged proximal different regions of the heat flux channel 110. For example, the first thermal spreader 126' can be arranged proximal a beginning region 112 of the heat flux channel 110, and the second thermal spreader 126" can be arranged proximal an end region 114 of the heat flux channel 110. Alternatively, multiple thermal spreaders 126 can be arranged proximal the same region of a heat flux channel 110. However, the thermal spreaders 126 can be positioned relative one another in any suitable configuration. The first and second thermal spreaders 126', 126" are preferably thermally connected. For example, the thermal spreaders 126 can be thermally connected by vias 122 positioned between the thermal spreaders 126. Alternatively, any suitable conductive material can be used to connect a plurality of heat spreaders. In a specific example, the thermal spreaders 126 are physically connected by vias 122 beginning or ending at either of the thermal spreaders 126. Alternatively, thermal spreaders 126 can be thermally insulated and/or isolated from each other. However, any number of thermal spreaders 126 can be configured in any suitable manner.

3.4 Supplemental Sensor

The system 100 can additionally or alternatively include one or more supplemental sensors, which can function to collect measurements indicating user sleep parameters, movement-related causes of transients in core body temperature measurements, cardiovascular parameters, and/or any suitable parameters. Supplemental sensors can include one or more of: motion sensors (e.g., accelerometers, gyroscopes, etc.), light sensors (e.g., infrared light sensor, photosensor, LED light sensor for photoplethysmography), bioelectrical signal sensors (e.g., ECG sensors, EEG, sensors, etc.), bioimpedance sensors (e.g., GSR sensors, EIT sensors), audio sensors, location sensors, and/or any other suitable sensors. In a specific example, the temperature monitoring device 105 can include an accelerometer electrically connected to a processing and control subsystem 130 mounted to the substrate 150, where the accelerometer is configured to collect measurements indicating user sleep parameters (e.g., user bodily configuration during sleep, time spent on back, left side, right side, stomach, etc.). In another example, the temperature monitoring device 105 can include a light sensor arranged proximal a user-facing region 144 of the housing 140, the light sensor configured to illuminate the target skin surface location and measure changes in light absorption for determining cardiovascular parameters (e.g., heart rate, heart rate variability, blood pressure, blood pressure variability, blood flow, heartbeat signatures, measures of blood vessel stiffness, measures indicative of atherosclerosis and/or other cardiovascular disease, etc.). However, the supplemental sensors can be configured in any suitable fashion.

3.5 Processing and Control Subsystem

The system 100 can additionally or alternatively include a processing and control subsystem 130, which functions to receive, process, and/or transmit data collected by the one or more temperature sensors 115. The processing and control subsystem 130 can additionally or alternatively function to control power provision and/or temperature sampling parameters. The processing and control subsystem 130 can additionally or alternatively include a processing module, communications module, and/or a power module. The processing and control subsystem 130 is preferably mounted to the substrate 150 and electrically connected to other components (e.g., temperature sensors 115, supplemental sensors, etc.), but can be located at any suitable location.

The processing and control subsystem 130 can include a processing module, which functions to process received data from the one or more temperature sensors 115. The processing module can additionally or alternatively function to control operation of components of the temperature monitoring device 105. The processing module of the processing and control subsystem 130 can include one or more: microprocessors, microcontrollers, central processing units, and/or other suitable processing devices. In a variation, the processing module is preferably configured to control sampling parameters associated with temperature data collected by the one or more temperature sensors 115 (e.g., sampling rate, when to sample, activation and deactivation of different temperature sensors 115, etc.). However, the processing module can be configured in any suitable manner.

The processing and control subsystem 130 can include a communications module, which functions to receive and/or transmit temperature-related data (e.g., temperature measurements, temperature sensor control instructions, etc.) and/or other suitable data. The communications module can include one or more: antennas, wired communication modules (e.g., communication pins, Ethernet components, powerline components, etc.), wireless communication modules (e.g., Bluetooth components such as Bluetooth Low Energy components, WiFi chips, Zigbee, Z-wave, radios, radiofrequency, infrared, magnetic induction, etc.) and/or any other suitable components. In an example, the temperature monitoring device 105 can include a wireless communication module at least partially encapsulated by the housing 140 and operable to transmit temperature data (e.g., sampled at the temperature sensors 115) to a remote processing system of the processing system (e.g., directly, such as through WiFi to the remote processing system for subsequent processing; server for subsequent processing; indirectly, such as through Bluetooth to a mobile computing device that transmits the data to the remote processing system; etc.), where the remote processing system can be operable to: determine a series of core body temperature measurements associated with a set of time periods corresponding to the temperature data; and detect a fever condition based on the series of core body temperature measurements (and/or the temperature data and/or any other associated parameters, etc.). In specific examples with a wired communication mechanism, the communication module can include wired contacts flush with an exterior surface of a housing 140, in order to facilitate a smooth housing surface that reduces the probability of the device catching onto clothing worn by a user. Alternatively, wired contacts can protrude from the housing 140, and/or be otherwise configured. Wired electrical contacts can cooperatively define an exterior surface (e.g., extend through; be integrated with; etc.) of the temperature monitoring device 105, and/or can be thermally connected to a thermal cage 120, a heat flux channel 110, and/or have any suitable relationship with other components. Components of the communications module are preferably arranged at locations with minimal EMI. For example, copper traces 190 of the substrate 150 are preferably etched at metal-free zones required for proper operation of an antenna, but communications module components can be positioned at any suitable location. Data transmitted by the communications module can be stored on memory (e.g., flash memory) included in the temperature monitoring device 105, but data from any suitable source can be transmitted. However, the communications module can be configured in any suitable fashion.

The processing and control subsystem 130 can include a power module, which functions to provide power to power-consuming components of the temperature monitoring device 105. The power module preferably includes a battery (e.g., a rechargeable battery such as a lithium chemistry battery, non-rechargeable battery, etc.) and a charging element, but can additionally or alternatively include any combination of suitable energy storage, generation, and/or conversion modules. The power module is preferably mounted to the substrate 150, facilitating power provision to the power-consuming components of the device. In a specific example, the power module is arranged adjacent a thermal cage 120, but can be otherwise located.

In a variation of the power module, the processing module can control power consumption to facilitate efficient power consumption, such as by powering temperature sensors 115 only when necessary for recording temperature measurements. However, the power module and/or components of the power module can be configured in any suitable manner.

3.6 Heat Collector.

The temperature monitoring device 105 can optionally include a heat collector 175, which functions to route heat (e.g., user body heat) into one or more heat flux channels 110. The heat collector 175 can additionally or alternatively function to facilitate charging of an energy storage device of the power module, to communicate data through induction, and/or to mechanically couple the temperature monitoring device 105 to a mounting system (e.g., a charging hub, a processing and control subsystem 130, casing, etc.). The heat collectors 175 preferably include one or more magnets, but can additionally or alternatively include electrical pins (e.g., pins that are environmentally exposed, flush with an exterior surface of the housing 140, protruding from the surface of the housing 140, etc.), piezoelectric devices, solar-charging devices, coiled wire (e.g., configured for inductive charging; electromagnetic coil; etc.), and/or any suitable heat collectors 175. The heat collector 175 is preferably constructed with thermally conductive materials (e.g., to facilitate heat routing), but can otherwise include any suitable materials. The heat collector 175 is preferably positioned between a heat source and a heat flux channel no. For example, the heat collector 175 can be positioned between an interior surface of the housing 140 and a temperature sensor 115 positioned at a beginning region 112 of a heat flux channel 110 (e.g., at a substrate inner layer), but the heat collector 175 can be otherwise located. In an example, the system 100 can include a thermally conductive heat collector 175 (e.g., a magnet and an electromagnetic coil operable to facilitate charging of a power module encapsulated by the housing 140, etc.) arranged between a user-facing region 144 of the housing 140 and a first temperature sensor 115' (e.g., arranged at a beginning region 112 of a heat flux channel no), where the thermally conductive heat collector 175 is operable to route heat from the measurement site to the heat flux channel no. In another example, the heat collector 175 can protrude from the housing 140 (e.g., an environmentally exposed heat collector 175 configured to serve as an electrical contact for recharging the power module). However, the heat collector 175 can be configured in any suitable manner.

3.7 Substrate

Figure 4A:
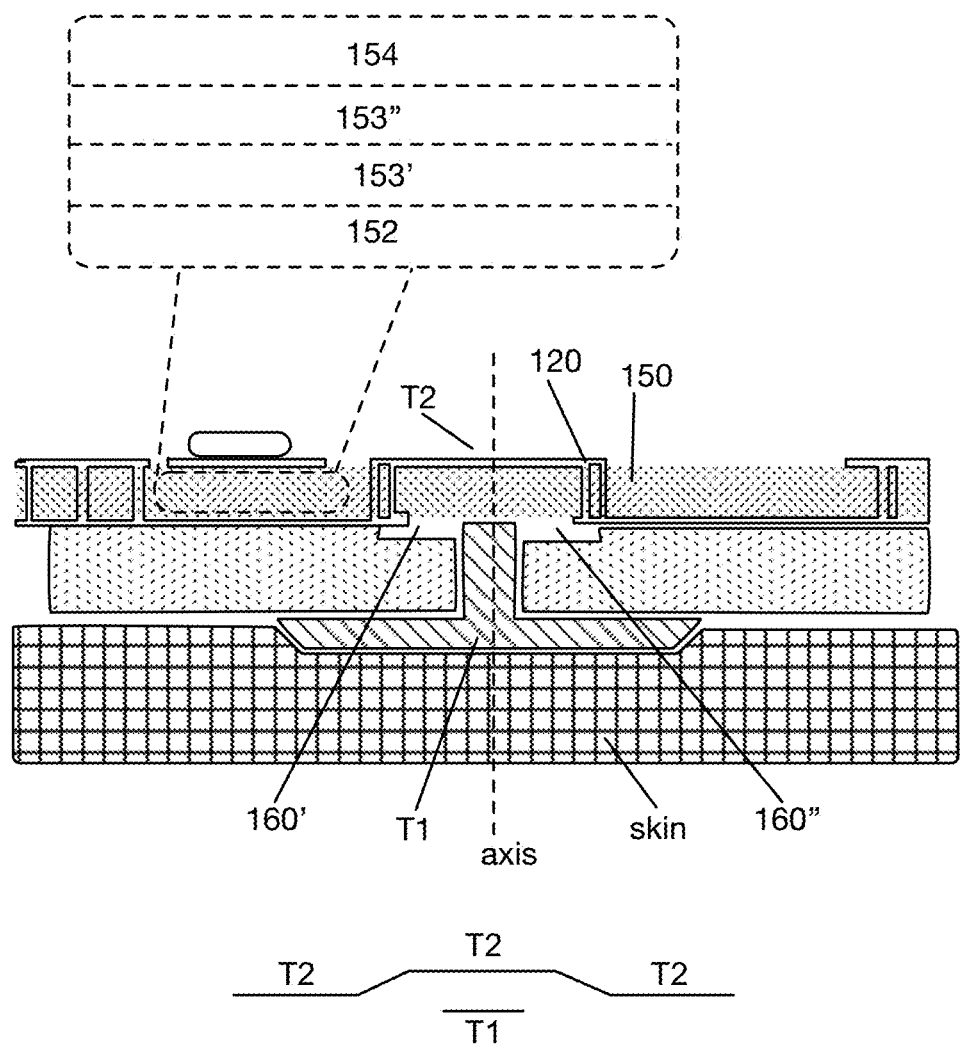
FIG. 4A-4B depict schematic representations of heat flow through a heat flux channel in a variation of a system for monitoring core body temperature.
Figure 4B:
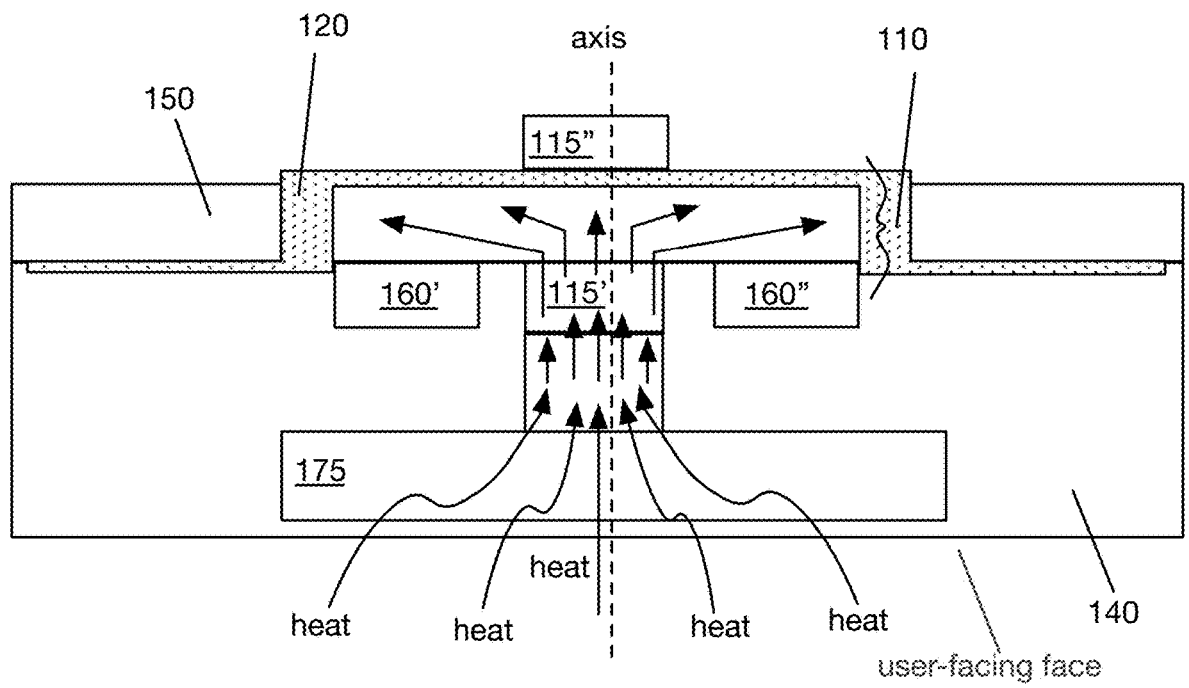

As shown in FIGS. 4A-4B, the temperature monitoring device 105 can additionally or alternatively include a substrate 150, which functions to provide a base of support (e.g., physical, electrical, thermal, etc.) and electrical connectivity for the components of the temperature monitoring device 105. The substrate 150 is preferably a printed circuit board (PCB), but can alternatively be any other suitable substrate type.

The substrate 150 can include a set of substrate layers (e.g., one or more substrate layers), which can include an outer substrate layer 154 (e.g., an environment-facing substrate layer), middle substrate layers 153', 153" and/or an inner substrate layer 152 (e.g., a user-facing substrate layer), but the substrate 150 can alternatively include a single layer and/or any other suitable layer(s). Additionally or alternatively, each substrate layer can include different regions including any one or more of: intermediary regions (e.g., proximal the center of the substrate 150; in between components arranged at the substrate 150; etc.), perimeter regions (e.g., proximal a perimeter and/or circumference of the substrate 150; etc.), and/or any other suitable regions.

In an example, the system 100 can include a substrate 150 physically supporting a first and a second set of temperature sensors 115 (e.g., thermally coupled to a first and a second heat flux channel 110', 110", respectively, etc.) and a first and a second thermal cage 120', 120", where the first and the second set of temperature sensors 115 each include: a beginning region temperature sensor 115 (e.g., a first beginning region temperature sensor 115' from the first set of temperature sensors; a second beginning region temperature sensor 115''' from the second set of temperature sensors; etc.) arranged at an inner layer of the substrate 150 proximal the first face 142 of the housing 140, and an end region temperature sensor 115 (e.g., a first end region temperature sensor 115" from the first set of temperature sensors; a second end region temperature sensor 115"" from the second set of temperature sensors; etc.) arranged at an outer layer of the substrate 150 distant the first face 142 of the housing 140; and where the first and the second thermal cages 120', 120" extend through the inner layer and the outer layer of the substrate 150. In another example, the system 100 can include, at the inner layer of the substrate 150, a first and a second thermal cage 120', 120" arcuately substantially encapsulating the respective beginning region temperature sensors 115 of the first and the second set of temperature sensors 115; where, at the outer layer of the substrate 150, the first and the second thermal cages 120', 120" arcuately substantially encapsulate the respective end region temperature sensors 115 of the first and the second set of temperature sensors 115. Additionally or alternatively, thermal cages 120' can be arranged in relation to heat flux channels 110 and/or associated temperature sensors 115 at any suitable portions of the substrate 150. In another example, the system 100 can include a supplemental temperature sensor 117 arranged between the first and the second heat flux channels 110', 110" at an intermediary region (and/or other suitable region) of the substrate 150, where the supplemental temperature sensor 117 is operable to measure a cross-talk-associated temperature during the time period, and where determination of the core body temperature can be based on the cross-talk-associated temperature (and/or other suitable data, such as heat flux channel temperature data). In another example, the system 100 can include a supplemental set of temperature sensors 117 arranged at different regions proximal a perimeter of the substrate 150 (e.g., separated by 120 degrees around the perimeter region of the substrate 150 for a set of three supplemental temperature sensors 117, etc.), where the supplemental set of temperature sensors 117 is operable to measure a heat gradient across the substrate 150, and where the determination of the core body temperature can be based on the heat gradient across the substrate 150 (and/or other suitable data, such as the cross-talk associated temperature data and heat flux channel temperature data, etc.). Additionally or alternatively, any suitable combination of components can be arranged at any suitable layers and/or regions of one or more substrates 150 defined by any suitable dimensions.

The substrate 150 is preferably constructed from glass-reinforced epoxy (e.g., FR-4, FR-1, FR-2, FR-3, FR-5, FR-6, G-10, G11, CEM-1, CEM-2, CEM-3, CEM-4, and/or CEM-5 grade materials, etc.), but can alternatively or additionally be constructed with epoxy resin, kapton, pyralux, pTFE (e.g., RF-35), alumina, polyimide, and/or other suitable materials. However, the substrate 150 can be configured in any suitable manner.

3.8 Thermal Gap Filler

The system 100 can additionally or alternatively include one or more thermal gap fillers 155, which function to promote heat flow through the one or more heat flux channels 110. The thermal gap fillers 155 can optionally be used to increase thermal connectivity between thermal components (e.g., be arranged between the inner and/or outer temperature sensor 115 and the heat flux channel 110, be arranged between the housing 140 and the heat collector 175, etc.). A thermal gap filler 155 is preferably thermally coupled to one or more temperature sensors 115 arranged at a heat flux channel 110. In an example, a thermal gap filler 155 can be situated in between a user-facing housing region (e.g., at an interior housing surface proximal a user's skin when the device is coupled to the user) and a temperature sensor 115 arranged at a beginning region 112 of a heat flux channel 110, thereby thermally connecting the temperature sensor 115 to the target user location. As shown in FIG. 4B, in a specific example, a thermal gap filler 155 can be positioned between a heat collector 175 and a temperature sensor 115 arranged at a beginning region 112 of a heat flux channel 110. In another example, a thermal gap filler 155 can be situated between a temperature sensor 115 arranged at an end region 114 of the heat flux channel 110 and an environment-facing housing region (e.g., at an interior housing surface proximal the environment when the device is coupled to the user). However, thermal gap fillers 155 can be arranged at any suitable location and/or be thermally connected to any suitable components. Thermal gap fillers 155 can be constructed with silicone (e.g., polysiloxane) and/or any suitable materials. However, thermal gap fillers 155 can be otherwise configured.

3.9 Thermal Insulation

The system 100 can additionally or alternatively include thermal insulation 160, which functions to thermally insulate one or more components of the temperature monitoring device 105. The thermal insulation 160 can additionally or alternatively function to restrict heat flow to flow through a thermal path. The thermal insulation 160 can include: air gaps (e.g., entraining air), vacuum chambers, thermally insulative foam, and/or any other suitable thermal insulation 160. In one example, the thermal insulation 16o can include air gaps, defined by the housing 140, in a location proximal the insulated component.

Figure 9:
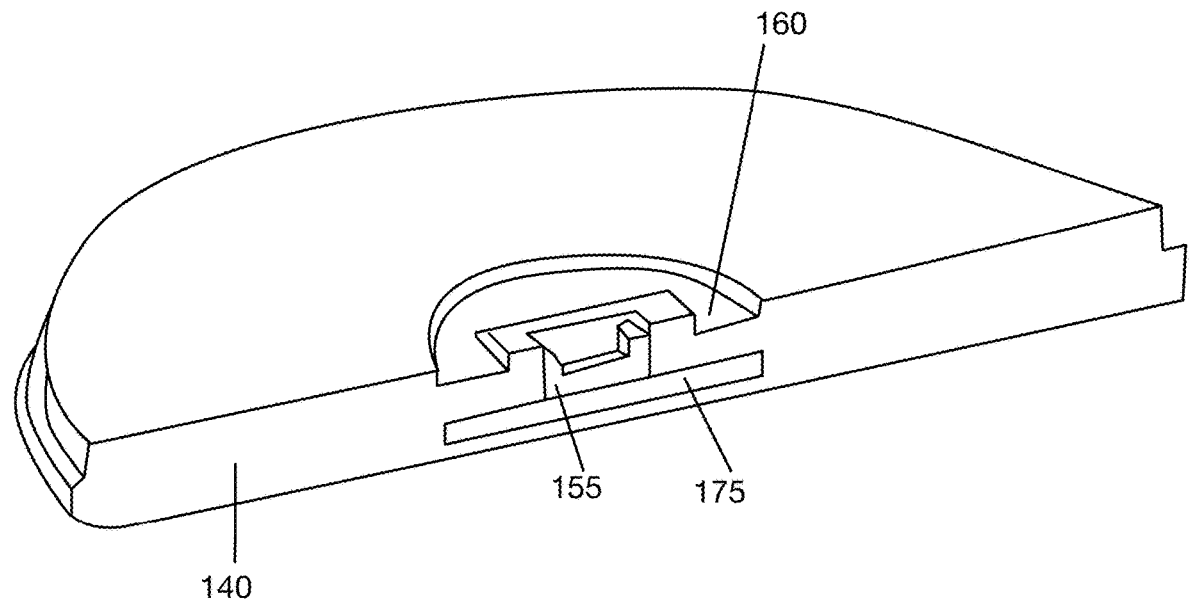
FIG. 9 depicts a schematic representation of a housing, charging element and thermal gap filler in a variation of a system for monitoring core body temperature.

The thermal insulation 16o preferably thermally insulates a segment of the thermally conductive path, but can alternatively thermally insulate and/or isolate portions of the housing 140 and/or any other suitable system component. For example, the thermal insulation 160 can be arranged along an exterior region of the thermal cage 120 (e.g., proximal the edges of the substrate 150), in order to separate the thermal cage 120 and thermal cage-encapsulated components from environmental heat. In another example, a thermal insulation 160 can be arranged proximal a beginning region 112 of a heat flux channel 110. In this example, the thermal insulation 160 can be physically contiguous with the beginning heat flux channel region and positioned radially inward from a thermal cage exterior perimeter (e.g., radially inward from a thermal spreader 126 of a thermal cage 120). However, a thermal insulation 160 can be thermally coupled, arranged at, and/or physically contiguous with any suitable component (e.g., heat flux channel 110, substrate 150, thermal cage 120, etc.), and/or otherwise positioned. Thermal insulation 160 can be of any suitable shape and size. In a specific example, as shown in FIG. 9, a thermal insulation 160 can possess an annular-ring shape. In another specific example, a thermal insulation 160 can be arranged around the entire perimeter of the thermal cage 120, defining a thermally insulating "moat" surrounding the thermal cage 120. In this specific example, thermally conductive bridges can optionally connect the materials on either side of the "moat", in order to provide connecting paths. A thermal insulation 160 is preferably filled with air (e.g., creating an air pocket 124), but can additionally or alternatively be filled with any suitable materials. In a specific example thermal insulations 160 (e.g., airpockets 124) can be arranged proximal a thermal gap filler, such as where each heat flux channel can be associated with a pair of thermal insulations (e.g., thermal insulations 160', 160'', 160''', 160'''', 160''''', 160'''''' for a tri-flux temperature monitoring device 105, etc.). However, thermal insulations 160 can be otherwise configured.

3.10 Housing

Figure 10:
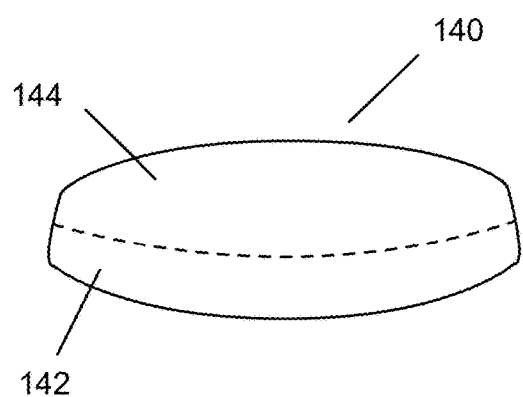
FIG. 10 depicts housing variations for a system for monitoring core body temperature.

As shown in FIGS. 9-10, the system 100 can additionally or alternatively include a housing 140, which functions to mechanically support and/or shield components of the temperature monitoring device 105. The housing 140 can optionally include a user-coupling mechanism.

The housing 140 preferably mechanically supports and/or encapsulates the one or more substrates 150, thermal cages 120, heat flux channels 110, and/or temperature sensors 115, but can otherwise house any suitable combination of components. The housing 140 preferably defines a user-facing region 144 (e.g., a region proximal the user's target skin surface location when the device is coupled to the user) and an environment-facing region (e.g., a region proximal the environment when the device is coupled to the user). User-facing regions 144 are preferably proximal to, include, define, and/or are otherwise associated with one or more measurement sites (e.g., corresponding to one or more heat flux channels 110, etc.). The housing 140 can additionally or alternatively define an interior surface (e.g., a surface facing components encapsulated by the housing 140) and an exterior surface (e.g., surface exposed to the environment and/or user skin surface). Components encapsulated by the housing 140 can be mounted to and/or physically connected to an interior housing surface, and mechanisms for coupling the device to the user can be mounted to and/or physically connected to an exterior housing surface. However, the housing 140 can define any suitable regions and/or surfaces.

Geometrically, the housing 140 preferably defines a disc-shaped form factor, but can additionally or alternatively define any suitable geometric shape. Additionally, the housing 140 preferably defines a thin side profile (e.g., configured to minimize lateral heat flow and/or shorten heat flux channel paths) and substantially circular broad faces. In an example, a set of temperature sensors 115 associated with a heat flux channel 110 can include: a beginning temperature sensor 115 arranged at a beginning region 112 of the first heat flux channel 110', where the beginning region 112 is proximal a first face 142 of the housing 140 (e.g., proximal and/or including a user-facing region 144, etc.), and an end temperature sensor 115 arranged proximal an end region 114 of the first heat flux channel 110', where the end region 114 is proximal a second face 144 (e.g., proximal and/or including a environment-facing region, etc.) opposite the first face 142 of the housing 140. In another example, the housing 140 can include a first substantially circular broad face including the user-facing region 144; and a second substantially circular broad face including the environment-facing region, where a thermally conductive path can substantially extend along an axis substantially perpendicular to the first and the second substantially circular broad faces, and/or can extend in any suitable orientation. However, the housing 140 can have any suitable geometric properties.

The housing 140 can optionally include a user-coupling mechanism, which functions to mount the temperature monitoring device 105 to a user body location. The user-coupling mechanism preferably includes one or more adhesives (e.g., double-sided disposable hypoallergenic adhesives), but can additionally or alternatively include a clip, mechanical fastener (e.g., latch, strap, rubber, etc.), an interference or friction fit, and/or other suitable adhesive. Adhesives are preferably attached to one or more exterior surfaces of a housing 140. However, any other suitable coupling mechanisms can be used.

The housing 140 is preferably constructed with materials possessing low thermal conductivity (e.g., Acrylonitrile-Butadiene-Styrene), hypoallergenic properties and/or any other suitable properties. The materials preferably provide a smooth, low-friction exterior surface of the housing 140, but the housing 140 can be constructed using any suitable combination of materials.

In examples, any components of the system 100 can define volumes including prisms, cubes, cylinders, spheres, and/or any suitable three-dimensional shape. Component surfaces can define rectangles, squares, circles, triangles, polygons, and/or other suitable shape. In relation to construction, any component can be constructed using any combination of materials including: metals (steel, copper tungsten, aluminum, etc.), plastics (e.g., acrylonitrile butadiene styrene, etc.), glass (e.g., fiberglass, etc.), elastomers (e.g., silicone rubber), polymers, and/or any other suitable materials.

Components of the system 100 can be manufactured using any one or more of: microlithography, doping, thin films, etching, bonding, polishing, patterning, deposition, microforming, treatments, drilling, plating, routing, and/or any other suitable manufacturing techniques. In a first example, a thermal cage 120 can be simultaneously fabricated (e.g., using stereolithography) with the substrate 150 (e.g., printed circuit board). In a second example, the substrate 150 can be manufactured, and the thermally insulative vias 122 can be subsequently drilled through one or more layers of the substrate 150, where the vias 122 can function as part of the thermal cage 120. In a third example, a heat flux channel no can be formed by fabricating the substrate 150, drilling at the target heat flux channel region, and filling the region with suitable material (e.g., thermally conductive material). Alternatively, a heat flux channel no can be formed through manufacturing the substrate 150 with inter-layer thermal connections. However, components of the system 100 can be otherwise assembled.

As a person skilled in the art will recognize from the previous detailed description and from the figure, modifications and changes can be made to the embodiments of the system without departing from the scope of the system.

Although omitted for conciseness, the preferred embodiments include every combination and permutation of the various system components and the various method processes, where the method processes can be performed in any suitable order, sequentially or concurrently.

As a person skilled in the art will recognize from the previous detailed description and from the figures and claims, modifications and changes can be made to the preferred embodiments of the invention without departing from the scope of this invention defined in the following claims.

We claim:

1. A system for monitoring core body temperature, the system comprising:
    a housing comprising a first face operable to couple to an external region of a user;
    a first and a second heat flux channel encapsulated by the housing and each defining a length extending along an axis non-parallel to the first face of the housing, wherein the first heat flux channel is associated with a first measurement site proximal a first region of the first face of the housing, and wherein the second heat flux channel is associated with a second measurement site proximal a second region of the first face of the housing;
    a first set of temperature sensors thermally coupled to the first heat flux channel and operable to measure first temperature data indicative of first temperature change through the first heat flux channel during a time period;
    a second set of temperature sensors thermally coupled to the second heat flux channel and operable to measure second temperature data indicative of second temperature change through the second heat flux channel during the time period;
    a first and a second thermal cage respectfully thermally coupled to and respectfully arranged around the first and the second heat flux channels along the lengths of the first and the second heat flux channels;
    a substrate physically supporting the first and the second set of temperature sensors and the first and the second thermal cages;
    wherein the first and the second set of temperature sensors each comprise:
        a beginning region temperature sensor arranged at an inner layer of the substrate proximal the first face of the housing, and
        an end region temperature sensor arranged at an outer layer of the substrate distant the first face of the housing;
    wherein the first and the second thermal cages extend through the inner layer and the outer layer of the substrate;
    a processing system operable to collect the first and the second temperature data for determination of a core body temperature associated with the time period; and
    a supplemental temperature sensor arranged between the first and the second heat flux channels at an intermediary region of the substrate, wherein the supplemental temperature sensor is operable to measure a cross-talk-associated temperature during the time period, and wherein the determination of the core body temperature comprises the determination based on the cross-talk-associated temperature and the first and the second temperature data.

2. The system of claim 1, further comprising:
    a third heat flux channel encapsulated by the housing and associated with a third measurement site proximal a third region of the first face of the housing;
    a third set of temperature sensors thermally coupled to the third heat flux channel and operable to measure third temperature data indicative of third temperature change through the third heat flux channel during the time period, wherein the determination of the core body temperature for the time period comprises the determination based on the first, the second, and the third temperature data.

3. The system of claim 2, wherein the first, second, and third heat flux channels are associated with a set of varying channel thermal resistances and a set of varying couplings to the processing system, and wherein the determination of the core body temperature for the time period comprises the determination based on the set of varying couplings, the set of varying channel thermal resistances, and the first, the second, and the third temperature data.

4. The system of claim 1,
    wherein, at the inner layer of the substrate, the first and the second thermal cages arcuately substantially encapsulate the respective beginning region temperature sensors of the first and the second set of temperature sensors;

wherein, at the outer layer of the substrate, the first and the second thermal cages at least partially encapsulate the respective end region temperature sensors of the first and the second set of temperature sensors.

5. The system of claim 1, further comprising a supplemental set of temperature sensors arranged at different regions proximal a perimeter of the substrate, wherein the supplemental set of temperature sensors is operable to measure a heat gradient across the substrate, and wherein the determination of the core body temperature comprises the determination based on the heat gradient across the substrate, the cross-talk-associated temperature, and the first and the second temperature data.

6. The system of claim 1, wherein the first and the second heat flux channels are respectfully associated with a first and a second channel thermal resistance, wherein the first and the second channel thermal resistances are different, and wherein the determination of the core body temperature comprises the determination based on the first and the second channel thermal resistances and the first and the second temperature data.

7. The system of claim 6, wherein the first and the second heat flux channels are respectfully associated with a first and a second coupling to an ambient environment, wherein the first and the second couplings are different, and wherein the determination of the core body temperature comprises the determination based on the first and the second couplings, the first and the second channel resistances, and the first and the second temperature data.

8. The system of claim 7, wherein the first set of temperature sensors comprises:
a beginning temperature sensor arranged at a beginning region of the first heat flux channel, wherein the beginning region is proximal the first face of the housing, and
an end temperature sensor arranged proximal an end region of the first heat flux channel, wherein the end region is proximal a second face opposite the first face of the housing; and wherein the system further comprises:
a heat sink thermally coupled to the end temperature sensor of the first set of temperature sensors, and wherein the heat sink is associated with the first coupling of the first heat flux channel to the processing system.

* * * * *